(12) United States Patent
Klaveness

(10) Patent No.: US 7,629,383 B2
(45) Date of Patent: Dec. 8, 2009

(54) DOUBLE ESTERS

(75) Inventor: Jo Klaveness, Oslo (NO)

(73) Assignee: Drug Discovery Laboratory AS, Oslo (NO)

( * ) Notice: Subject to any disclaimer, the term of this patent is extended or adjusted under 35 U.S.C. 154(b) by 740 days.

(21) Appl. No.: 10/496,328

(22) PCT Filed: Nov. 22, 2002

(86) PCT No.: PCT/GB02/05305

§ 371 (c)(1),
(2), (4) Date: May 18, 2005

(87) PCT Pub. No.: WO03/045893

PCT Pub. Date: Jun. 5, 2003

(65) Prior Publication Data

US 2005/0203181 A1 Sep. 15, 2005

(30) Foreign Application Priority Data

Nov. 22, 2001 (GB) ................................ 0128052.8

(51) Int. Cl.
*A61K 31/225* (2006.01)
*C07C 69/52* (2006.01)
(52) U.S. Cl. ..................................... 514/547; 560/199
(58) Field of Classification Search ................. 514/547; 560/199
See application file for complete search history.

(56) References Cited

U.S. PATENT DOCUMENTS

| 4,462,934 A | 7/1984 | Jasys |
| 4,545,784 A * | 10/1985 | Sanderson ............... 8/107 |

FOREIGN PATENT DOCUMENTS

| EP | 0122763 A2 | 10/1984 |
| EP | 0122763 A3 | 10/1984 |
| EP | 0122763 B1 | 10/1984 |
| EP | 0125781 A1 | 11/1984 |
| EP | 0125781 B1 | 11/1984 |
| FR | 2616430 * | 6/1988 |
| JP | 59-216891 | 12/1984 |
| JP | 11-029527 | 2/1999 |
| WO | WO 92/17436 | 10/1992 |
| WO | WO 93/17718 | 9/1993 |

OTHER PUBLICATIONS

Wilkerson, Michael G. and Wilkin, Jonathan K., Azelaic Acid Esters Do Not Depigment Pigmented Guinea Pig Skin, Archives of Dermatology 126 (1990) 252-253.

* cited by examiner

*Primary Examiner*—Taylor Victor Oh
(74) *Attorney, Agent, or Firm*—Kenyon & Kenyon LLP

(57) ABSTRACT

The invention provides acyloxymethyl esters of $C_{6-14}$ alkanedicarboxylic acids, or physiologically tolerable salts or esters thereof, for use in medicine as therapeutic or prophylactic agents.

13 Claims, No Drawings

DOUBLE ESTERS

This application is a U.S. national stage application of PCT international application number PCT/GB02/05305, and claims the benefit of priority of PCT international application number PCT/GB02/05305, which was filed on Nov. 22, 2002, designating the United States of America and published in English, the entire contents of which are hereby expressly incorporated by reference in their entirety.

This invention relates to certain double ester compounds, their preparation and their use, in particular by topical, oral or parenteral administration as antibiotics or in the treatment of cancer.

Various alkane-dicarboxylic acids are known to have biological properties useful in therapy and prophylaxis. One example of such a dicarboxylic acid is the linear alkane-α,ω-dicarboxylic acid known as azelaic acid ($C_9H_{16}O_4$—nonanedioic acid or heptane-1,7-dicarboxylic acid). The primary medical use of azelaic acid is in the treatment of acne where it is applied topically in the form of a 20% cream (e.g. Skinoren®, available from Schering AG, Berlin, Germany).

Topical application of azelaic acid helps to normalise keratinisation and to reduce proliferation of *Propionibacterium acne*, i.e. it exhibits both anti-inflammatory and antibiotic properties. Moreover, unlike many antibiotics, it does not induce bacterial resistance.

Clinical studies have shown azelaic acid to have other beneficial therapeutic effects. Thus for example it is relatively effective in the treatment of papulopustular rocasea, in the treatment of hyperpigmentation, as an antibacterial against *Staphylococcus epidermidis* and *Staphylococcus aureus*, as an antimycotic agent against *Candida albicans, Candida glabrata, Pityrosporum ovale* and against species of *Trichophyton*, and as an antitumor agent or as an enhancer of cytotoxicity of other anti-cancer agents, in the treatment of androgenetic alopecia, etc.

However azelaic acid has relatively low efficacy in topical treatment of acne (for which reason it is present in the very high concentration of 20% in the commercially available creams—most dermatological creams contain less than 5% of their active ingredient) and local adverse effects, e.g. a burning sensation, are not uncommon.

Azelaic acid moreover has relatively poor biological uptake and bioelimination properties. Thus administered topically only about 3.6% of the dose is absorbed, while administered orally only about 60% is absorbed. Furthermore 60% of absorbed azelaic acid is excreted into the urine within 12 hours.

There is thus a need for improved ways of presenting azelaic acid, in particular ways which would enable the required dosages and/or treatment times to be reduced.

It has been proposed to administer azelaic acid and other dicarboxylic acid drug compounds in the form of their esters; however there are no reports of such esters as having been demonstrated to have beneficial properties, indeed Wilkerson et al. reported in Arch. Dermatol. 126: 252-253 (1990) that azelaic acid esters did not depigment guinea pig skin.

We have now surprisingly found that alkane-dicarboxylic acid double esters have improved properties relative to the alkane-dicarboxylic acid itself.

A double ester is a term used for a compound containing an acyloxymethyloxycarbonyl group and such compounds are also referred to as acetal esters.

One double ester of azelaic acid is known from the literature as an activator for hydrogen peroxide in bleach compositions—this is bis(1-(acetyloxy)ethyl)-nonanedioate (see EP-A-125781 and EP-A-122763). This double ester is not however described as having any pharmaceutical utility.

Thus viewed from one aspect the invention provides acyloxymethyl esters of $C_{6-14}$ alkane-dicarboxylic acids, or physiologically tolerable salts or esters thereof, for use in medicine as therapeutic or prophylactic agents.

Viewed from a further aspect the invention provides acyloxymethyl esters of $C_{6-14}$ alkane-dicarboxylic acids, other than bis(1-(acetyloxy)ethyl)nonanedioate, and physiologically tolerable salts and esters thereof.

The term acyl as used herein means a group attached via an oxo-substituted atom, preferably a carbon atom, e.g. a carbonyl-attached group. The atom α to the carbonyl group is preferably carbon but may also be oxygen; i.e. the term "acyloxymethyl" may include alkoxycarbonyloxymethyl. In the compounds of the invention the acyl group preferably contains 2 to 16 carbon atoms.

The alkane-dicarboxylic acids used in the present invention are $C_6$ to $C_{14}$ dicarboxylic acids, in particular $C_8$ to $C_{10}$ dicarboxylic acids, especially $C_9$ dicarboxylic acids. The molecular backbone linking the carboxyl groups may be linear, branched or cyclic or a mixture thereof; however it is especially preferred that the acids be n-alkane-α-ω-dioic acids, i.e. with carboxyl groups at either end of a linear $(CH_2)_n$ group.

In a preferred embodiment therefore the compounds of the invention are compounds of formula I

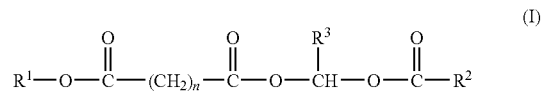

(where n is an integer having a value of 4 to 12, preferably 6, 7 or 8, most preferably 7;

$R^1$ is hydrogen, an optionally substituted, optionally unsaturated $C_{1-15}$ alkyl group, or, preferably, a group —$CHR^3$—O—CO—$R^2$;

each $R^2$ independently is an optionally substituted, optionally unsaturated $C_{1-15}$ alkyl or alkoxy group or together with the $R^3$ γ to it is a 2 to 5 backbone atom bridging group;

and each $R^3$ independently is hydrogen, an optionally substituted, optionally unsaturated $C_{1-15}$ alkyl group, a group $R^2$—CO—O— or together with $R^2$ forms a bridging group as defined above), and physiologically tolerable salts thereof.

In the compounds of formula I, $R^2$ may also represent an aryl, aralkyl, alkaryl, aryloxy, aralkoxy or alkaryloxy group (especially an aryl or aralkyl group) containing up to 16 carbons, e.g. a phenyl, benzyl, etc group.

The alkyl groups in the compounds of formula I are preferably branched, linear or cyclic $C_{1-7}$, more preferably $C_{1-6}$, alkyl groups and may be optionally substituted, e.g. with one or more hydroxyl groups, oxo groups, halo atoms (e.g. F or Cl), alkoxy groups (e.g. $C_{1-6}$ alkoxy groups), acyloxy (e.g. $C_{1-6}$ alkanoyloxy) groups, thiol groups, amino groups, aromatic groups (e.g. $C_{6-10}$ aryl groups), alkylthio (e.g. $C_{1-6}$ alkylthio) groups, alkylamino (e.g. $C_{1-6}$ alkylamino or N—($C_{1-6}$ alkyl)-$C_{1-6}$-alkylamino) groups, etc.

Preferred examples of $R^3$ groups include hydrogen, methyl, ethyl, propyl and bridging groups, especially hydrogen and methyl. Preferred examples of $R^2$ groups include methyl, ethyl, propyl, butyl (e.g. n-butyl or t-butyl), pentyl, benzyl, methoxy, ethoxy, propyloxy, butoxy, pentoxy, benzyloxy, phenyl and heptyl. Preferred examples of $R^1$ groups include $C_{1-10}$ alkyl (especially methyl and ethyl) and —$CHR^3$—O—CO—$R^2$ groups, especially the latter.

Especially preferably in the compounds of formula I n is 7, 8, 9 or 10; $R^2$ is $C_{2-6}$ alkyl or alkoxy or phenyl; $R^3$ is H or methyl; and $R^1$ is $CH_3$ or $CHR^3OCOR^2$.

Examples of particularly preferred compounds of formula I include the following:
bis[(acetyloxy)methyl]hexanedioate
bis[(trifluoroacetyloxy)methyl]hexanedioate
bis[(propionyloxy)methyl]hexanedioate
bis[(butyryloxy)methyl]hexanedioate
bis[(2,2-dimethylpropionyloxy)methyl]hexanedioate
bis[phenylacetyloxy)methyl]hexanedioate
bis[(stearoyloxy)methyl]hexanedioate
bis[(methoxycarbonyloxy)methyl]hexanedioate
bis[(ethoxycarbonyloxy)methyl]hexanedioate
bis[(phenylmethoxycarbonyloxy)methyl]hexanedioate
bis[1-(acetyloxy)ethyl]hexanedioate
bis[1-(trifluoroacetyloxy)ethyl]hexanedioate
bis[1-(propionyloxy)ethyl]hexanedioate
bis[1-(butyryloxy)ethyl]hexanedioate
bis[(2,2-dimethylpropionyloxy)ethyl]hexanedioate
bis[1-(phenylacetyloxy)ethyl]hexanedioate
bis[1-(stearoyloxy)ethyl]hexanedioate
bis[1-(methoxycarbonyloxy)ethyl]hexanedioate
bis[1-(ethoxycarbonyloxy)ethyl]hexanedioate
bis[benzoyloxymethyl]hexanedioate
bis[hexanoyloxymethyl]hexanedioate
bis[octanoyloxymethyl]hexanedioate
hexanedioic acid 2,2-dimethylpropionyloxymethyl ester methyl ester
hexanedioic acid 1-ethoxycarbonyloxy-ethyl ester methyl ester
bis[(acetyloxy)methyl]heptanedioate
bis[(trifluoroacetyloxy)methyl]heptanedioate
bis[(propionyloxy)methyl]heptanedioate
bis[(butyryloxy)methyl]heptanedioate
bis[(2,2-dimethylpropionyloxy)methyl]heptanedioate
bis[phenylacetyloxy)methyl]heptanedioate
bis[(stearoyloxy)methyl]heptanedioate
bis[(methoxycarbonyloxy)methyl]heptanedioate
bis[(ethoxycarbonyloxy)methyl]heptanedioate
bis[(phenylmethoxycarbonyloxy)methyl]heptanedioate
bis[1-(acetyloxy)ethyl]heptanedioate
bis[1-(trifluoroacetyloxy)ethyl],heptanedioate
bis[1-(propionyloxy)ethyl]heptanedioate
bis[1-(butyryloxy)ethyl]heptanedioate
bis[(2,2-dimethylpropionyloxy)ethyl]heptanedioate
bis[1-(phenylacetyloxy)ethyl]heptanedioate
bis[1-(stearoyloxy)ethyl]heptanedioate
bis[1-(methoxycarbonyloxy)ethyl]heptanedioate
bis[1-(ethoxycarbonyloxy)ethyl]heptanedioate
bis[1-(phenylmethoxycarbonyloxy)ethyl]heptanedioate
bis[benzoyloxymethyl]heptanedioate
bis[hexanoyloxymethyl]heptanedioate
bis[octanoyloxymethyl]heptanedioate
heptanedioic acid 2,2-dimethylpropionyloxymethyl ester methyl ester
heptanedioic acid 1-ethoxycarbonyloxy-ethyl ester methyl ester
bis[(acetyloxy)methyl]octanedioate
bis[(trifluoroacetyloxy)methyl]octanedioate
bis[(propionyloxy)methyl]octanedioate
bis[(butyryloxy)methyl]octanedioate
bis[(2,2-dimethylpropionyloxy)methyl]octanedioate
bis[phenylacetyloxy)methyl]octanedioate
bis[(stearoyloxy)methyl]octanedioate
bis[(methoxycarbonyloxy)methyl]octanedioate
bis[(ethoxycarbonyloxy)methyl]octanedioate
bis[(phenylmethoxycarbonyloxy)methyl]octanedioate
bis[1-(acetyloxy)ethyl]octanedioate
bis[1-(trifluoroacetyloxy)ethyl]octanedioate
bis[1-(propionyloxy)ethyl]octanedioate
bis[1-(butyryloxy)ethyl]octanedioate
bis[(2,2-dimethylpropionyloxy)ethyl]octanedioate
bis[1-(phenylacetyloxy)ethyl]octanedioate
bis[1-(stearoyloxy)ethyl]octanedioate
bis[1-(methoxycarbonyloxy)ethyl]octanedioate
bis[1-(ethoxycarbonyloxy)ethyl]octanedioate
bis[1-(phenylmethoxycarbonyloxy)ethyl]octanedioate
bis[benzoyloxymethyl]octanedioate
bis[hexanoyloxymethyl]octanedioate
bis[octanoyloxymethyl]octanedioate
octanedioic acid 2,2-dimethylpropionyloxymethyl ester methyl ester
octanedioic acid 1-ethoxycarbonyloxy-ethyl ester methyl ester
bis[(acetyloxy)methyl]nonanedioate
bis[(trifluoroacetyloxy)methyl]nonanedioate
bis[(propionyloxy)methyl]nonanedioate
bis[(butyryloxy)methyl]nonanedioate
bis[(2,2-dimethylpropionyloxy)methyl]nonanedioate
bis[phenylacetyloxy)methyl]nonanedioate
bis[(stearoyloxy)methyl]nonanedioate
bis[(methoxycarbonyloxy)methyl]nonanedioate
bis[(ethoxycarbonyloxy)methyl]nonanedioate
bis[(phenylmethoxycarbonyloxy)methyl]nonanedioate
bis[1-(acetyloxy)ethyl]nonanedioate
bis[1-(trifluoroacetyloxy)ethyl]nonanedioate
bis[1-(propionyloxy)ethyl]nonanedioate
bis[1-(butyryloxy)ethyl]nonanedioate
bis[(2,2-dimethylpropionyloxy)ethyl]nonanedioate
bis[1-(phenylacetyloxy)ethyl]nonanedioate
bis[1-(stearoyloxy)ethyl]nonanedioate
bis[1-(methoxycarbonyloxy)ethyl]nonanedioate
bis[1-(ethoxycarbonyloxy)ethyl]nonanedioate
bis[1-(phenylmethoxycarbonyloxy)ethyl]nonanedioate
bis[benzoyloxymethyl]nonanedioate
bis[hexanoyloxymethyl]nonanedioate
bis[octanoyloxymethyl]nonanedioate
nonanedioic acid 2,2-dimethylpropionyloxymethyl ester methyl ester
nonanedioic acid 1-ethoxycarbonyloxy-ethyl ester methyl ester
bis[(acetyloxy)methyl]decanedioate
bis[(trifluoroacetyloxy)methyl]decanedioate
bis[(propionyloxy)methyl]decanedioate
bis[(butyryloxy)methyl]decanedioate
bis[(2,2-dimethylpropionyloxy)methyl]decanedioate
bis[phenylacetyloxy)methyl]decanedioate
bis[(stearoyloxy)methyl]decanedioate
bis[(methoxycarbonyloxy)methyl]decanedioate
bis[(ethoxycarbonyloxy)methyl]decanedioate
bis[(phenylmethoxycarbonyloxy)methyl]decanedioate
bis[1-(acetyloxy)ethyl]decanedioate
bis[1-(trifluoroacetyloxy)ethyl]decanedioate
bis[1-(propionyloxy)ethyl]decanedioate
bis[1-(butyryloxy)ethyl]decanedioate
bis[(2,2-dimethylpropionyloxy)ethyl]decanedioate
bis[1-(phenylacetyloxy)ethyl]decanedioate
bis[1-(stearoyloxy)ethyl]decanedioate
bis[1-(methoxycarbonyloxy)ethyl]decanedioate
bis[1-(ethoxycarbonyloxy)ethyl]decanedioate bis[1-(phenylmethoxycarbonyloxy)ethyl]decanedioate
bis[benzoyloxymethyl]decanedioate
bis[hexanoyloxymethyl]decanedioate
bis[octanoyloxymethyl]decanedioate
decanedioic acid 2,2-dimethylpropionyloxymethyl ester methyl ester
decanedioic acid 1-ethoxycarbonyloxy-ethyl ester methyl ester
bis[(acetyloxy)methyl]undecanedioate
bis[(trifluoroacetyloxy)methyl]undecanedioate
bis[(propionyloxy)methyl]undecanedioate
bis[(butyryloxy)methyl]undecanedioate
bis[(2,2-dimethylpropionyloxy)methyl]undecanedioate
bis[phenylacetyloxy)methyl]undecanedioate
bis[(stearoyloxy)methyl]undecanedioate
bis[(methoxycarbonyloxy)methyl]undecanedioate
bis[(ethoxycarbonyloxy)methyl]undecanedioate
bis[(phenylmethoxycarbonyloxy)methyl]undecanedioate
bis[1-(acetyloxy)ethyl]undecanedioate
bis[1-(trifluoroacetyloxy)ethyl]undecanedioate
bis[1-(propionyloxy)ethyl]undecanedioate
bis[1-(butyryloxy)ethyl]undecanedioate
bis[(2,2-dimethylpropionyloxy)ethyl]undecanedioate
bis[1-(phenylacetyloxy)ethyl]undecanedioate
bis[1-(stearoyloxy)ethyl]undecanedioate
bis[1-(methoxycarbonyloxy)ethyl]undecanedioate
bis[1-(ethoxycarbonyloxy)ethyl]undecanedioate
bis[1-(phenylmethoxycarbonyloxy)ethyl]undecanedioate
bis[benzoyloxymethyl]undecanedioate
bis[hexanoyloxymethyl]undecanedioate
bis[octanoyloxymethyl]undecanedioate
undecanedioic acid 2,2-dimethylpropionyloxymethyl ester methyl ester
undecanedioic acid 1-ethoxycarbonyloxy-ethyl ester methyl ester
bis[(acetyloxy)methyl]dodecanedioate
bis[(trifluoroacetyloxy)methyl]dodecanedioate
bis[(propionyloxy)methyl]dodecanedioate
bis[(butyryloxy)methyl]dodecanedioate
bis[(2,2-dimethylpropionyloxy)methyl]dodecanedioate
bis[phenylacetyloxy)methyl]dodecanedioate
bis[(stearoyloxy)methyl]dodecanedioate
bis[(methoxycarbonyloxy)methyl]dodecanedioate
bis[(ethoxycarbonyloxy)methyl]dodecanedioate
bis[(phenylmethoxycarbonyloxy)methyl]dodecanedioate
bis[1-(acetyloxy)ethyl]dodecanedioate
bis[1-(trifluoroacetyloxy)ethyl]dodecanedioate
bis[1-(propionyloxy)ethyl]dodecanedioate
bis[1-(butyryloxy)ethyl]dodecanedioate
bis[(2,2-dimethylpropionyloxy)ethyl]dodecanedioate
bis[1-(phenylacetyloxy)ethyl]dodecanedioate
bis[1-(stearoyloxy)ethyl]dodecanedioate
bis[1-(methoxycarbonyloxy)ethyl]dodecanedioate
bis[1-(ethoxycarbonyloxy)ethyl]dodecanedioate
bis[1-(phenylmethoxycarbonyloxy)ethyl]dodecanedioate
bis[benzoyloxymethyl]dodecanedioate
bis[hexanoyloxymethyl]dodecanedioate
bis[octanoyloxymethyl]dodecanedioate
dodecanedioic acid 2,2-dimethylpropionyloxymethyl ester methyl ester, and
dodecanedioic acid 1-ethoxycarbonyloxy-ethyl ester methyl ester The compounds of the invention or for use in the invention can be prepared using standard processes and procedures well-known in the art for derivatization of multi-functional compounds, and especially esterification and more especially formation of acyloxymethyl esters.

As known in the literature, esterification of compounds may desirably involve protection and deprotection of appropriate groups; for example using technology described by McOmie in "Protective Groups in Organic Chemistry", Plenum 1973 and T. W. Greene in "Protective Groups in Organic Chemistry", Wiley-Interscience 1981. Starting materials for preparation of double esters of dicarboxylic acids according to the invention are typically the corresponding dicarboxylic acids or derivatives thereof. Some examples of dicarboxylic acids or derivatives thereof well known in the prior art and suitable for use as starting materials for synthesis of double esters according to the present invention include:
adipic acid,
pimelic acid,
suberic acid,
azelaic acid,
sebacic acid,
undecanedioic acid,
dodecanedioic acid,
1,11-undecanedicarboxylic acid, and
1,12-dodecanedicarboxylic acid, all of which are commercially available through Sigma-Aldrich.

Some dicarboxylic acid derivatives useful as intermediates in synthesis of dicarboxylic acids according to the present invention include:
adipic acid monomethyl ester,
adipic acid monoethyl ester,
suberic acid monomethyl ester,
azelaic acid monomethyl ester, and
sebacic acid monoethyl ester (all available through Sigma-Aldrich),
azelaic acid dicaesium salt (see Cimecioglu et al., Makromol. Chem. Rapid Commun. 10: 319-324 (1989)), and azelaic acid monoethyl ester.

Viewed from a further aspect, the present invention thus provides a process for the preparation of a compound according to the invention, said process comprising reacting a $C_{6-14}$ alkane-dicarboxylic acid or a salt or ester thereof, with an acyloxymethylating agent.

Examples of acyloxymethylating agents include compounds of formula II

$$R^2—CO—O—CHR^3—X \quad (II)$$

where $R^2$ and $R^3$ are as hereinbefore defined and X is a leaving group, e.g. a halogen atom, a hydroxyl group, a sulphonic acid ester group, etc.

Preferably the compound of formula II is reacted with a salt of a dicarboxylic acid, e.g. a caesium salt, with a dicarboxylic acid in which one of the carboxyl groups is in a protected form (e.g. esterified), or with a dicarboxylic acid in which one or both carboxyl groups is in an activated form (e.g. acid halide form).

Thus for example the compound of formula II may be reacted with a compound of formula III

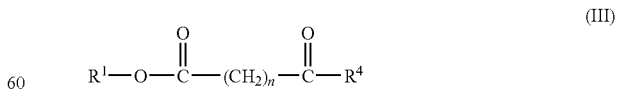

(where $R^1$ and n are as hereinbefore defined and $R^4$ is a hydroxy or halo group) or a salt thereof.

The reactions may conventionally be carried out in a solvent or mixture of solvents such as acetone, diethylether, dimethylformamide, dimethylsulphoxide etc. at temperatures up to boiling point of the mixture, preferably at ambient temperatures. The conditions of the esterification reactions will depend on the reagents used and the conditions may be chosen such that maximum yield of the double ester is obtained.

As mentioned earlier, the compounds of the invention or for use according to the invention may be in the form of pharmaceutically acceptable salts. Such salts can be acid addition salts with physiologically acceptable organic or inorganic acids if the compound according to the present invention has one or more basic group, or can be base addition salts with physiologically acceptable organic or inorganic bases. Typically appropriate acids include hydrochloric acid, hydrobromic acid, lactic acid, citric acid, methane sulfonic acid, maleic acid, fumaric acid, and stearinic acid. Typically appropriate bases include sodium hydroxide, potassium hydroxide, calcium hydroxide and meglumine.

Procedures for salt formation are well described in scientific literature and patent literature.

As mentioned above, the compounds of the invention and for use according to the invention and their salts have valuable pharmacological properties. The compounds can be used for treatment of acne, rocasea, hyperpigmentation, wound healing, actinic keratoses, basal cell carcinoma and other dermal disease conditions. In particular the compounds may be used to delay or prevent relapse of basal cell carcinoma following treatment with photodynamic therapy. The compounds can also be used to treat bacterial, viral and fungal infections and can also be used in treatment or prevention of cancer.

Viewed from a further aspect therefore the invention provides a method of treatment of a human or non-human (e.g. mammalian) animal subject to combat a condition susceptible to treatment with a $C_{6-14}$ alkane-dicarboxylic acid drug substance, the improvement comprising administering to said subject an effective amount of said drug substance in the form of an acyloxymethyl ester thereof.

Viewed from a still further aspect the invention provides the use of an acyloxymethyl ester of a $C_{6-14}$ alkane-dicarboxylic acid drug substance or a salt or ester thereof for the manufacture of a medicament for use in a method of treatment of a human or non-human (e.g. mammalian) animal subject to combat a condition susceptible to treatment with said dicarboxylic acid drug substance.

The compositions of the invention may be formulated in conventional manner with one or more physiologically acceptable carriers or excipients, according to techniques well known in the art. Viewed from a still further aspect therefore the invention provides a pharmaceutical composition comprising an acyloxymethyl ester of a $C_{6-14}$ alkane-dicarboxylic acid or a physiologically tolerable salt or ester thereof together with at least one pharmaceutical carrier or excipient.

When appropriate, the compositions according to the invention may be sterilized, e.g. by γ-radiation, strike filtration, autoclaving or heat sterilization, before or after formulation with carrier or excipient.

The compounds according to the invention can also be formulated together with other pharmacologically active substances. Selection of such substances will be dependent on the indication for the composition. A composition for treatment of acne might be a formulation of one or more of the compounds according to this invention together with for example benzoyl peroxide, clindamycin, tretinoin, erythromycin, tetracyclins, adapalene, tazarotene, sulfectamide or other antiacne agents. A composition for treatment of rocasea might be a formulation of one or more of the compounds according to this invention together with other compounds effective for treatment of rocasea; for example tetracyclins or metronidazole. Compositions for treatment of hyperpigmentation could be formulated as a mixture of one or more of compounds according to the present invention together with glycolic acid, hydroquinone or other agents active against hyperpigmentation of skin.

Compositions for treatment of infections (e.g. bacterial, fungal and viral infections) might contain in addition to one or more of the compounds according to the present invention, other pharmacologically active antiinfective agents; for example compositions for treatment of bacterial infections might contain penicillins, cephalosporins, peptide antibiotics, macrolide antibiotics, antibacterial sulphonamides, vancomycin or other antibacterial agents, for example compounds described by Norrby, R. in Expert Opin. Pharmacother. 2001, 2, 293-302, Wada, K. et al in Nippon Rinsho 2001, 59, 790-94, Grandi, G. in Trends Biotechnol. 2001, 19, 181-88, Guay, D. R. in Drugs 2001, 61, 353-64, Kopp-Hoolihan, L. In J. Am. Diet. Assoc. 2001, 101, 229-38 and 239-41, Robert, P. Y. et al in Drugs 2001, 61, 175-85, Fulton, B. et al in Paediatr. Drugs 2001, 3, 137-58, Bhanot, S. K. et al in Curr. Pharm. Des. 2001, 7, 311-35, Krasemann, C. et al in Clin. Infect Dis. 2001, 32 Supplement S51-63, Bush, K. et al in Curr. Opin. Investig. Drugs 2000, 1, 22-30, Rubin, B. K. et al in Curr. Opin. Investig. Drugs 2000, 1, 169-72, Leung, W. K. et al in Expert Opin. Pharmacother. 2000, 1, 507-14, Periti, P. in Expert Opin. Pharmacother. 2000, 1, 1203-17, Anonymous in Nat. Biotechnol. 2000, 18 Supplement, IT 24-6, Dbaibo, G. S. in J. Med. Liban. 2000, 48, 177-81, Muller, M. et al in Cell. Mol. Life Sci. 1999, 56, 280-5, Gray, C. P. et al in Cell Mol. Life-Sci. 1999, 56, 779-87, Bax, R. et al in Int. J. Antimicrob. Agents 2000, 16, 51-9 and Bush, K. et al in Curr. Opin. Chem. Biol. 2000, 4, 433-9 or in references therein.

Compositions according to the present invention for treatment of fungal infections might for example contain nystatin, amphothericin, griseofulvin, imidazole derivatives and triazole derivatives like chlotriamazole, micronazole, econazole, ketoconazole and bifonazole and other agents like, for example, antifungal agents described by Espinel-Ingroff, A. et al in Mycopathologica 2001, 150, 101-15, Yang, Y. L. et al in J. Microbiol. Immunol. Infect. 2001, 34, 79-86, Willems, L. et al in J. Clin. Pharm. Ther. 2001, 26, 159-69, Worthen, D. R. et al in Drug Dev. Ind. Pharm. 2001, 27, 277-186, Dupont, B. in Rev. Prat. 2001, 51, 752-7, Kauffman, C. A. in AIDS Patient Care STDS II Supplement 1, S18-21, Rex, J. H. et al in Clin. Infect. Dis. 2001, 32, 1191-200, Hann, I. M. et al in Int. J. Antimicrob. Agents 2001, 17, 161-9, Arikan, S. et al in Curr. Pharm. Des. 2001, 7, 393-415, Kroting, H. C. et al in Hautarzi 2001, 52, 91-7, Fringuelli, R. et al in J. Chemother. 2001, 13, 9-14, Anonymous in Nat. Biotechnol. 2000, 18, Suppl. IT 24-6, Ellepola, A. N. et al in Dent. Update 2000, 27, 165-70 and 172-4, Ellepola, A. N. et al in Dent. Update 2000, 27, 111-2 and 114-6, Neely, M. N. et al in Eur. J. Microbiol. Infect. Dis. 2000, 19, 897-914, Walsh, T. J. et al in Med. Mycol. 2000, 38, Suppl. 1, 335-47, Graybill, J. R. et al in Med. Mycol. 2000, 38, Suppl. 1, 323-33 and Fingquelievich, J. L. et al in Med. Mycol. 2000, 38 Suppl. 1, 317-22 or in references therein.

Compositions according to the present invention for treatment of viral infections might for example contain agents for treatment of DNA viruses or RNA viruses. Typical such compounds that could be included in compositions according to the present invention can be acyclovir, ganciclovir, valaciclovir, ribavirin, foscarnet, protease inhibitors like saquinavir, indinavir, ritonavir and nelfinavir, reverse transcriptase inhibitors like zidovudine, didanosine, zulcitabine, stavudine, lamivudine, abakavir, nevirapine and etavirenze and neuramidase inhibitors like zanamivire or other antiviral agents, for example agents described by Delaney, W. E. et al in Antivir. Chem. Chemother, 2001, 12, 1-35, Buss, N. et al in Antivir. Ther. 2001, 6, 1-7, Roberts, N. A. et al in Prog. Drug Res. 2001, 56, 195-237, Field, H. J. in J. Clin. Virol. 2001, 21, 261-9, Bowers, M. in BETA 1996, Jun. 19-22, Mediratta, P. K. et al in Indian J. Med. Sci. 2000, 54, 485-90, Fleming, D. M. in Int. J. Clin. Pract. 2001, 55, 189-35, Mahalingam, S. et al in Bioessays 2001, 23, 428-35, Nabel. G. J. in Nature 2001, 410 (6831), 1002-7, Lever, A. M. in Sex Transm. Infect. 2001, 77, 93-6, McClellan et al in Drugs 2001, 61, 263-843 and Brown, T. J. et al in Dermatol. Clin. 2001, 19, 23-34 and references therein.

A composition for treatment or prevention of cancer-related diseases might for example be a formulation of one or more of the compounds according to this invention together with other agents for treatment of prevention of cancer. Typical substances for treatment of cancer could for example be alkylating agents like for example cyclophosphamide, chlorambucile, melfalane, iphosphamide, treosulfane, tiotepa, carmustine, iomustine, fotemustine, temozolomide, antimetabolites like for example metotrexate, raltitrexed, mercaptopurine, clodribine, fludarabine, cytarabine, fluorouracil, gemcitabin, plant alkaloides and other natural products like for example vinblastine, vincristine, vinorelbine, etoposid, paclitaxel, docetaxel, cytotoxic antibiotics like for example daktinomycine, doxorubicine, daunorubicine, epirubicine, idarubicine, mitoxantrone, bleomycine, plikamycine, mitomycine and other cytotoxic agents like for example cisplatin, carboplatin, amsakrine, altretamine, estramustine, topotecane, irinotecane, verteporfine, hormones, hormone-like substances and other substances described by Stachel, S. J. et al in Curr. Pharm. Des. 2001, 7, 1277-90, Gueritte, F. in Curr. Pharm. Des. 2001, 7, 1229-1249, de Groot, F. M. et al in Curr. Med. Chem. 2001, 8, 1093-1122, Sebti, S. M. et al in Oncogene 2000, 19, 6584-93, Ramirez De Molina, A. et al in Int. J. Oncol. 2001, 19, 5-17, Crul, M. et al in Anticancer Drugs 2001, 12, 163-84, Chamberlain, R. S. et al in Expert Opin. Pharmacother. 2000, 1, 603-14, Rowley, P. T. et al in Anticancer Res. 2000, 20, 4419-29, Schirner, M. in Cancer Metastasis Rev. 2000, 19, 67-73, Hofman, J. in Rev. Physiol. Biochem. Pharmacol. 2001, 142, 1-96, Goss, P. E. et al in J. Clin. Oncol. 2001, 19, 881-94, Hadi, S. M. et al in IUBMB Life 2000, 50, 167-71, Perry, P. J. et al in Expert Opin. Investig. Drugs 1999, 8, 1981-2008, Koki, A. T. et al in Expert Opin, Investig. Drugs 1999, 8, 1623-1638 and Kushner, D. M. et al in Curr. Oncol. Rep. 2000, 2, 23-30 and references therein.

Typical substances for prevention of cancer which might be included in the compositions of the invention could for example be Vitamin E and other agents with antioxidative properties and COX-2 inhibitors.

The compositions according to the invention may be administered topically, orally, rectally or systemically depending on the indication and choice of substance or substances.

The compositions may be presented in a form adapted for enteral or parenteral administration. Compositions for enteral administration can for example be plain or coated tablets, sustained release tablets, soft capsules, hard capsules, suppositories, suspensions and solutions of the active component (s) optionally together with one or more inert conventional carriers.

Compositions for parenteral administration could for example be formulations for intradermal, subcutaneous, intraperitoneal or intravenous injection or infusion. Other parenteral compositions include compositions for topical administration; including compositions for administration not only to skin but to mucosa and administered to hair. Such topical compositions include gels, creams, ointments, shampoos, soaps, spray, lotions, salves, aerosols and other pharmaceutical formulations for topical use.

All compositions might optionally be formulated with one or more inert carriers and/or diluents; e.g. water, water/ethanol, ethanol, water/glycerol, polyethyleneglycol, sodium chloride, glucose, sucrose, lactose, corn starch, microcrystalline cellulose, sorbitol, magnesium stearate, alcohols, polyvinylpyrroidone, fatty acids, fat, fat wax, EDTA and calcium chloride.

The compositions may additionally include wetting agents, lubrication agents, emulsifying agents, suspending agents, preserving agents, sweetening agents, flavoring agents and absorption enhancers.

The compositions may be in the form of microemulsions, nanoparticles, microspheres, niosomes or liposomes.

Compositions in which the drug substance is in a non-aqueous environment (e.g. an ointment) are especially preferred.

The concentration of the active compound(s) as described hereinbefore in the compositions, depends upon several factors, including mode of administration, chemical nature of the compounds, clinical indication and condition of the patient. The concentration will therefore vary over a large range. Generally, however, active agent concentration ranges of 0.005 to 100%, e.g. 0.01 to 70%, commercially 0.05 to 50%, and preferably 0.1 to 20% (w/w) are suitable. Typically compositions with high concentrations of dicarboxylic acid double esters (>10%) according to the present invention will include oral products like capsules or tablets, while other composition forms will normally have lower concentration (<10%) of the active compound(s).

The compositions according to the present invention are preferably in a ready to use form; however concentrates and kits may also be used. Such a kit might contain two or more containers, e.g.

a) a first container containing a dicarboxylic acid double ester or a pharmaceutically acceptable salt thereof; and b) a second container containing a solvent for dissolution or dispersion of the contents of the first container prior to use.

This kit formulation might typically be used where the dicarboxylic acid double ester or other pharmaceutically active substances in the composition are unstable in a ready to use formulation (e.g. shelf life is less than 6 months or preferably less than 12 months).

It is believed that presentation as an acyloxymethyl ester may be beneficial for other dicarboxylic acid drug substances, especially those with poor transdermal uptake or rapid urinary excretion and the invention is deemed to extend to other dicarboxylic acid drug substances, especially alkane, azaalkane, thiaalkane and oxaalkane dicarboxylic acids.

The invention will now be described in more detail in the following non-limiting Examples:

Synthesis of Chloromethyl Ester Starting Materials

Chloromethyl pivalate and 1-chloroethyl ethyl pivalate are commercially available. Other chloromethyl esters were synthesised by reacting paraformaldehyde with acid chlorides.

EXAMPLE A

Synthesis of Chloromethyl Benzoate

Benzoyl chloride (14.05 g, 0.10 mol) and paraformaldehyde (3.6 g, 0.12 mol) were heated at 120° C. until the latter disappeared (about 2 hours). The reaction mixture was distilled in vacuo and chloromethyl benzoate was obtained as a colourless oil (b.p. 116° C., 10 mbar). $^{1}$H-NMR (CDCl$_3$) δ

8.18-7.46 (m, 5H), 6.00 (s, 2H). $^{13}$C-NMR (CDCl$_3$) δ 133.89, 131.36, 130.01, 128.91, 128.54, 69.21.

EXAMPLE B

Synthesis of Chloromethyl Butyrate

Butyryl chloride (10.65 g, 0.10 mol) and paraformaldehyde (3.60 g, 0.12 mol) were heated at 120° C. until the latter disappeared (about 2 hours). The reaction mixture was distilled in vacuo and chloromethyl butyrate was obtained as a colourless oil (b.p. 90° C., 25 mbar). $^1$H-NMR (CDCl$_3$) δ 5.67 (s, 2H), 2.37-2.29 (m, 2H), 1.64-1.58 (m, 2H), 1.26 (s, 8H).

EXAMPLE C

Synthesis of Chloromethyl Hexanoate

Thionyl chloride (14.27 g, 0.12 mmol) was added dropwise to hexanoic acid (11.61 g, 0.10 mmol) and the reaction mixture was heated at 70° C. for 24 hours. The reaction mixture containing hexanoyl chloride was not further purified and paraformaldehyde (3.60 g, 0.12 mol) was added and the reaction mixture heated at 120° C. until the latter disappeared (about 2 hours). The reaction mixture was distilled in vacuo and chloromethyl hexanoate was obtained as a colourless oil (b.p. 118° C., 25 mbar). $^1$H-NMR (CDCl$_3$) δ 5.67 (s, 2H), 2.37-2.29 (m, 2H), 1.65-1.58 (m, 2H), 1.31-1.26 (m, 4H), 0.88 (t, 3H). $^{13}$C-NMR(CDCl$_3$) δ 179.89, 171.77, 68.53, 33.95, 31.18, 24.34, 22.26, 13.83.

EXAMPLE D

Synthesis of Chloromethyl Octanoate

Octanoyl chloride (16.26 g, 0.10 mol) and paraformaldehyde (3.6 g, 0.12 mol) were heated at 120° C. until the latter disappeared (about 2 hours). The reaction mixture was distilled in vacuo and chloromethyl octanoate was obtained as a colourless oil (b.p. 140° C., 25 mbar). $^1$H-NMR (CDCl$_3$) δ 5.67 (s, 2H), 2.37-2.29 (m, 2H), 1.64-1.58 (m, 2H), 1.26 (s, 2H), 0.84 (t, 3H). $^{13}$C-NMR(CDCl$_3$) δ 171.75, 162.30, 68.51, 33.94, 31.55, 28.97, 28.85, 28.80, 24.64, 24.50, 22.52, 13.98.

EXAMPLE E

Synthesis of Hexyl 2-Chloroacetate

Chloroacetoyl chloride (2.48 g, 22.00 mmol) in CH$_2$Cl$_2$ (10 ml) was added dropwise to a solution of hexan-1-ol (2.04 g, 20.00 mmol) and triethylamine (2.22 g, 22.00 mmol) in CH$_2$Cl$_2$ (25 ml). The reaction mixture was stirred at room temperature for 3 hours, evaporated in vacuo and then diluted with diethyl ether (25 ml). The organic layer washed with saturated NaHCO$_3$ (3×10 ml), dried with MgSO$_4$ and filtered. Evaporation in vacuo gave the product as a red oil. $^1$H-NMR (CDCl$_3$) δ 4.01 (s, 2H), 1.63-1.53 (m, 2H), 1.28-1.13 (m, 8H), 0.85 (t, 3H). $^{13}$C-NMR(CDCl$_3$) δ 167.36, 66.36, 40.86, 31.28, 28.36, 25.36, 22.43, 13.88.

General Procedure for the Synthesis of Esters of Alkanedioic Acids

A heterogeneous solution of Cs$_2$CO$_3$, NaI (as catalyst) and alkanedioic acid in THF was stirred for ½ hour at 60° C. A chloroalkylester in THF was added dropwise to the solution and stirred at 60° C. for 48 hours. The reaction mixture was cooled to room temperature, evaporated in vacuo and diethyl ether was added to the residue. The organic layer was washed with saturated NaHCO$_3$, filtered and dried with MgSO$_4$. Evaporation in vacuo gave the expected product.

EXAMPLE 1

Bis[[(2,2-dimethylpropanoyl)oxy]methyl]nonanedioate (Compound I)

Caesium carbonate (32.6 g; 0.120 mol) was added to a stirred solution of nonanedioic acid (9.4 g; 50.0 mmol), chloromethyl pivalate (15.1 g; 0.10 mmol), and NaI (0,5 g; 3.3 mmol) in dry N,N-dimethylformamide (50 mL). The mixture was stirred for 2 days at ca. 40° C. (bath temperature) under argon. Excess solvent was evaporated off at ca. 35° C. (bath temperature) and 5 to 1 mm Hg. The residue was dissolved in water (50 mL) and diethyl ether (25 mL). The aqueous portion was extracted with ether (1×15 mL) and the combined ether solutions were washed with saturated NaCl solution (1×10 mL) and dried (Na$_2$SO$_4$). Filtration and evaporation left 12.34 g (59%) after pumping out to 0.2 mm Hg. $^1$H NMR (200 MHz; CDCl$_3$): δ 1.20 (20H, s), 1.32 (4H, s), 1.63 (4H, m), 2.35 (4H, t, J=7.4 Hz), 5.76 (4H, d, J=2.8 Hz). $^{13}$C NMR (50 MHz; CDCl$_3$): δ 24.58, 26.84, 28.80, 29.01, 33.92, 38.73, 79.22, 164.87, 172.29, MS(ES):439.3 [M+Na]$^+$.

EXAMPLE 2

Creams Containing Compound I

Three creams containing compound I (2%, 5% and 10% w/w) from Example 1 were prepared by mixing in compound I in Unguentum Merck® using a mortar and pestle.

EXAMPLE 3

Clinical Testing of Creams from Example 2

Indication: Acne Rocasea

A 47 year old male patient with more than 20 years history of Acne Rocasea in the face (more than 20 cm$^2$ located below eyes and around nose) administered 10% cream (Example 2) twice daily (morning and evening). The symptoms were reduced after 2-3 days and the patient was free from visual symptoms after 1 week of treatment. The patient continued to use 2% cream once every 2-3 weeks and has been free from symptoms for 9 months. The patient had previously used oral oxytetracycline capsules and 1% metronidazole cream with no major clinical effect.

EXAMPLE 4

Clinical Testing of Creams from Example 2

Indication: Wound Healing

A 77 year old male patient with several wounds and extreme dry skin in the forehead and scalp had tried out different moisturizers without any healing effect. After approximately one week of daily treatment with 2% cream (Example 2), the patient observed a normalization of the skin with only two wounds left. The patient observed some new formation of hair at the area of treatment.

EXAMPLE 5

Ointment Containing Compound I

An ointment containing 10% wt of Compound I from Example 1 was prepared by mixing compound I and a water-free ointment base (Vaseline®/albumin) in a pestle and mortar.

EXAMPLE 6

Synthesis of bis-[[2,2-dimethylpropionyl]oxymethyl] dodecanedioate

A heterogeneous solution of $Cs_2CO_3$ (13.03 g, 40 mmol), NaI (200 mg, 1.3 mmol) and dodecanedioic acid (4.60 g, 20 mmol) in THF (40 ml) was stirred for ½ hour at 60° C. Chloromethyl pivalate (6.02 g, 40 mmol) in THF (10 ml) was added dropwise to the solution and stirred at 60° C. for 48 hours. The reaction mixture was cooled to room temperature and evaporated in vacuo. Diethyl ether (50 ml) was added and the residue was washed with saturated $NaHCO_3$ (3×25 ml), dried with $MgSO_4$ and filtered. Evaporation in vacuo gave the product as a colourless oil (5.13 g, 56.0%). MS (ES): 481.4 $[M+Na]^+$. $^1$H-NMR ($CDCl_3$) δ 5.95 (s, 4H), 2.51-2.47 (m, 4H), 1.58-1.52 (m, 4H), 1.21-1.15 (m, 30H). $^{13}$C-NMR δ 176.30, 172.50, 79.13, 38.69, 33.91, 29.26, 28.87, 26.76, 25.54, 24.61.

EXAMPLE 7

Synthesis of bis-[1-[ethoxycarbonyloxy]-ethyl]nonanedioate

A heterogeneous solution of $Cs_2CO_3$ (13.03 g, 40 mmol), NaI (200 mg, 1.3 mmol) and nonanedioic acid (3.76 g, 20 mmol) in THF (40 ml) was stirred for % hour at 60° C. 1-Chloroethyl ethyl carbonate (6.10 g, 40 mmol) in THF (10 ml) was dropwise added to the solution and stirred at 60° C. for 48 hours. The reaction mixture was cooled to room temperature and evaporated in vacuo. Diethyl ether (50 ml) was added and the residue was washed with saturated $NaHCO_3$ (3×25 ml), dried with $MgSO_4$ and filtered. Evaporation in vacuo gave the product as a yellow oil (3.83 g, 45.6%). $^1$H-NMR ($CDCl_3$) δ 6.39 (q, 2H), 4.26-4.16 (m, 4H), 2.31-2.25 (m, 4H)1.55-1.58 (m, 4H), 1.46 (d, 2H), 1.32-1.18 (m, 12H). $^{13}$C-NMR ($CDCl_3$) δ 178.35, 171.63, 152.97, 91.08, 64.89, 33.91, 28.75, 24.53, 19.49, 14.04.

EXAMPLE 8

Synthesis of Bis-[1-[ethoxycarbonyloxy]ethyl]dodecanedioate

A heterogeneous solution of $Cs_2CO_3$ (13.03 g, 40 mmol), NaI (200 mg, 1.3 mmol) and dodecandioic acid (4.60 g, 20 mmol) in THF (40 ml) was stirred for ½ hour at 60° C. 1-Chloroethyl ethyl carbonate (6.10 g, 40 mmol) in THF (10 ml) was added dropwise added to the solution and stirred at 60° C. for 48 hours. The reaction mixture was cooled to room temperature and evaporated in vacuo. Diethyl ether (50 ml) was added and the residue washed with saturated $NaHCO_3$ (3×25 ml), dried with $MgSO_4$ and filtered. Evaporation in vacuo gave the product as a yellow oil (4.25 g, 47.5%). $^1$H-NMR ($CDCl_3$) δ 8.39 (q, 2H), 6.27-6.10 (m, 4H), 4.35-4.24 (m, 4H), 3.60-3.57 (4H), 3.46-3.43 (d, 6H), 3.32-3.22 (m, 18H).

EXAMPLE 9

Synthesis of nonanedioic acid 2,2-dimethyl-propionyloxymethyl ester methyl ester A heterogeneous solution of $Cs_2CO_3$ (1.30 g, 4.0 mmol), NaI (30 mg, 0.20 mmol) and nonanedioic acid monomethyl ester (0.95 g, 4.0 mmol) in THF (15 ml) was stirred for ½ hour at 60° C. Chloromethyl pivalate (0.60 g, 4.0 mmol) in THF (5 ml) was added dropwise to the solution and stirred at 60° C. for 48 hours. The reaction mixture was cooled to room temperature and evaporated in vacuo. Diethyl ether (25 ml) was added, and the residue was washed with saturated $NaHCO_3$ (3×15 ml), dried with $MgSO_4$ and filtered. Evaporation in vacuo gave the product as a colourless oil (0.85 g, 67.5%). $^1$H-NMR ($CDCl_3$) δ 5.74 (s, 2H), 3.66 (s, 3H), 2.38-2.26 (m, 4H), 1.63-1.56 (m, 4H), 1.31 (s, 6H), 1.21 (s, 9H). $^{13}$C-NMR ($CDCl_3$) δ 177.05, 174.06, 172.23, 79.19, 51.33, 38.63, 33.90. 33.82, 28.78, 28.72, 28.64, 26.74, 24.73, 24.47.

EXAMPLE 10

Synthesis of nonanedioic acid 1-(ethoxycarbonyloxy)-ethyl ester methyl ester

A heterogeneous solution of $Cs_2CO_3$ (1.30 g, 4.0 mmol), NaI (30 mg, 0.20 mmol) and nonanedioic acid monomethyl ester (0.95 g, 4.0 mmol) in THF (15 ml) was stirred for ½ hour at 60° C. 1-Chloroethyl ethyl carbonate (0.61 g, 4.0 mmol) in THF (5 ml) was added dropwise to the solution and stirred at 60° C. for 48 hours. The reaction mixture was cooled to room temperature and evaporated in vacuo. Diethyl ether (25 ml) was added and the residue was washed with saturated $NaHCO_3$ (3×25 ml), dried with $MgSO_4$ and filtered. Evaporation in vacuo gave the product as a colourless oil (0.96 g, 75.1%). $^1$H-NMR ($CDCl_3$) δ 6.74 (q, 1H), 4.19 (q, 2H), 3.64 (s, 3H), 2.34-2.24 (m, 4H), 1.63-1.53 (m, 4H), 1.49 (d, 2H), 1.33-1.24 (m, 9H). $^{13}$C-NMR ($CDCl_3$) δ 174.55, 172.04, 162.92, 153.39, 91.48, 64.75, 51.79, 36.85, 34.37, 31.78, 29.24, 25.19, 24.82, 19.09, 14.48.

EXAMPLE 11

Synthesis of bis-(benzoyloxymethyl) nonanedioate

A heterogeneous solution of $Cs_2CO_3$ (3.25 g, 10.00 mmol), NaI (50 mg, 0.33 mmol) and nonanedioic acid (0.94 g, 5.00 mmol) in THF (20 ml) was stirred for ½ hour at 60° C. Chloromethyl benzoate (1.70 g, 10 mmol) in THF (10 ml) was added dropwise to the solution and stirred at 60° C. for 48 hours. The reaction mixture was cooled to room temperature and evaporated in vacuo. Diethyl ether (25 ml) was added and the residue was washed with saturated $NaHCO_3$ (3×15 ml), dried with $MgSO_4$ and filtered. Evaporation in vacuo gave the product as a white solid (1.76 g, 77.2%). $^1$H-NMR ($CDCl_3$) δ 8.09-7.39 (m, 10H), 5.97 (s 4H), 2.37-2.29 (m, 4H), 1.61-1.56 (m, 4H), 1.28-1.25 (m, 6H). $^{13}$H-NMR ($CDCl_3$) δ 172.65, 165.20, 133.63, 130.01, 128.92, 128.44, 79.71, 33.84, 28.70, 28.65, 24.42.

EXAMPLE 12

Synthesis of bis-(butanoyloxymethyl)nonanedioate

A heterogeneous solution of $Cs_2CO_3$ (2.60 g, 8.00 mmol), NaI (30 mg, 0.20 mmol) and nonanedioic acid (0.94 g, 4.00 mmol) in THF (15 ml) was stirred for ½ hour at 60° C. Chloromethyl butanoate (1.09 g, 8.00 mmol) in THF (5 ml) was added dropwise added to the solution and stirred at 60° C. for 48 hours. The reaction mixture was cooled to room temperature and evaporated in vacuo. Diethyl ether (25 ml) was added and the residue was washed with saturated NaHCO₃ (3×05 ml), dried with MgSO₄ and filtered. Evaporation in vacuo gave the product as a colourless oil (0.76 g, 49.0%). ¹H-NMR (CDCl₃) δ 5.70 (s, 4H), 2.29 (t, 8H), 1.65-1.55 (m, 8H), 1.27 (s, 6H), 0.90 (t, 6H). ¹³C-NMR (CDCl₃) δ 172.31, 162.50, 78.97, 35.73, 33.81, 28.67, 24.41, 18.05, 13.43.

EXAMPLE 13

Synthesis of bis-(hexanoyloxymethyl) nonanedioate

A heterogeneous solution of Cs₂CO₃ (1.30 g, 4.00 mmol), NaI (20 mg, 0.13 mmol) and nonanedioic acid (0.37 g, 2.00 mmol) in THF (15 ml) was stirred for % hour at 60° C. Chloromethyl hexanoate (0.65 g, 4.00 mmol) in THF (5 ml) was added dropwise added to the solution and stirred at 60° C. for 48 hours. The reaction mixture was cooled to room temperature and evaporated in vacuo. Diethyl ether (20 ml) was added and the residue was washed with saturated NaHCO₃ (3×10 ml), dried with MgSO₄ and filtered. Evaporation in vacuo gave the product as a colourless oil (0.91 g, 51.9%). ¹H-NMR (CDCl₃) δ 5.72 (s, 4H), 2.43-2.32 (m, 8H), 1.75-1.64 (m, 8H), 1.36-1.33 (m, 14H), 0.91 (t, 6H). ¹³C-NMR (CDCl₃) δ 172.80, 162.72, 79.40, 34.49, 34.30, 34.25, 31.51, 29.19, 29.12, 24.85, 24.66, 22.62, 14.22.

EXAMPLE 14

Synthesis of bis-(octanoyloxymethyl) nonanedioate

A heterogeneous solution of Cs₂CO₃ (2.60 g, 4.00 mmol), NaI (30 mg, 0.20 mmol) and nonanedioic acid (0.75 g, 4.00 mmol) in THF (20 ml) was stirred for ½ hour at 60° C. Chloromethyl octanoate (1.53 g, 8.00 mmol) in THF (5 ml) was added dropwise added to the solution and stirred at 60° C. for 48 hours. The reaction mixture was cooled to room temperature and evaporated in vacuo. Diethyl ether (20 ml) was added and the residue was washed with saturated NaHCO₃ (3×15 ml), dried with MgSO₄ and filtered. Evaporation in vacuo gave the product as a colourless oil (0,95 g, 47.9%). ¹H-NMR (CDCl₃) δ 5.76 (s, 4H), 2.37 (t, 8H), 1.65 (t, 8H), 1.30 (s br, 22H), 90 (t, 6H). ¹³C-NMR (CDCl₃) δ 172.89, 62.32, 79.44, 34.35, 34.26, 31.99, 29.32, 29.23, 29.14, 24.99, 24.86, 22.94, 14.41.

EXAMPLE 15

Antibacterial Activity of Azelaic Acid and Azelaic Acid Derivatives

The antibacterial effects of azelaic acid and the azelaic acid derivatives of Examples 7, 12 and 13 on *Staphylococcus aureus* were tested on agar gels. All the derivatives showed large inhibiting zones while azelaic acid in the same amount (10 mg) showed no inhibiting effect.

The derivatives showed also high activity against *Enterococcus faecalis, Streptococcus pyogenes* and *Staphylococcus epidermida*.

EXAMPLE 16

Clinical Testing of Creams of Example 2

Indication: Skin Cancer

A 76 year old woman with skin cancer in the face (one lesion above the nose) was treated with photodynamic therapy (5-ALA methyl ester, available from Photocure ASA, Oslo, Norway). The outcome of the treatment was very good. After about one year she observed a new lesion in the same area. She has now been using a 5% cream (Example 2) on a weekly basis for about 1.5 years to keep the development of the disease under control.

EXAMPLE 17

Clinical Testing of Creams from Example 2

Safety

The cream of Example 2 has been tested for treatment of various skin diseases for about 2 years (see previous Examples). No local or systemic side effects have been observed. The patient from Example 3 has been treated on a daily basis for weeks with the cream (2-10%) without any sign of toxicity.

The invention claimed is:

1. A compound of formula I

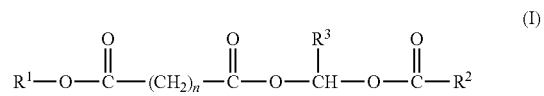

where n is an integer having a value of 5 to 12;

R¹ is an optionally unsaturated C₁₋₁₅ alkyl group optionally substituted with one or more of hydroxyl groups, oxo groups, halogenyl groups, alkoxy groups, acyloxy groups, thiol groups, amino groups, alkylthio groups, and alkylamino groups, or is a group —CHR³—O—CO—R²;

each R² independently is an optionally unsaturated C₁₋₁₅ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the R³ gamma to it is a 2 to 5 backbone atom bridging group;

and each R³ independently is hydrogen, an optionally unsaturated C₁₋₁₅ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group R²—CO—O— or together with R² forms a 2 to 5 backbone atom bridging group, or a physiologically tolerable salt thereof, provided that the compound of formula I is not bis(1-(acetyloxy)ethyl) nonanedioate.

2. The compound of claim 1 wherein n is 6, 7 or 8, R¹ is a C₁₋₁₀ alkyl group or a group of formula —CHR³—O—CO—R², R³ is hydrogen or a C₁₋₃ alkyl group, and each R² is a methyl, ethyl, propyl, butyl, pentyl, benzyl, methoxy, ethoxy, propyloxy, butoxy, pentoxy or benzyloxy group, or a physiologically tolerable salt thereof.

3. The compound of claim 1 wherein n is 7, 8, 9 or 10; R² is C₂₋₆ alkyl or alkoxy or phenyl; R³ is H or methyl; and R¹ is CH₃ or CHR³OCOR², or a physiologically tolerable salt thereof.

4. The compound of claim 1 wherein n is 6, 7 or 8.

5. The compound of claim 1 wherein n is 7.

6. A process for the preparation of a compound according to claim 1, said process comprising reacting a C₅₋₁₂ alkanedicarboxylic acid or a salt or ester thereof, with an acyloxymethylating agent.

7. The process of claim 6, said process comprising reacting a compound of formula III

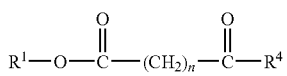 (III)

where n is an integer having a value of 5 to 12, $R^1$ is an optionally unsaturated $C_{1-15}$ alkyl group optionally substituted with one or more of hydroxyl groups, oxo groups, halogenyl groups, alkoxy groups, acyloxy groups, thiol groups, amino groups, alkylthio groups, and alkylamino groups, or is a group —$CHR^3$—O—CO—$R^2$;

$R^2$ is an optionally unsaturated $C_{1-15}$ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the $R^3$ gamma to it is a 2 to 5 backbone atom bridging group;

and $R^3$ independently is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group $R^2$—CO—O— or together with $R^2$ forms a bridging group, and $R^4$ is a hydroxy or halo group; or a salt thereof with an acyloxymethylating agent of formula II $R^2$—CO—O—$CHR^3$—X (II)

wherein $R^2$ is an optionally unsaturated $C_{1-15}$ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the $R^3$ gamma to it is a 2 to 5 backbone atom bridging group;

and $R^3$ independently is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group $R^2$—CO—O— or together with $R^2$ forms a bridging group; and X is a leaving group.

8. The process of claim 7, wherein the leaving group is a halogen atom, a hydroxyl group, or a sulphonic acid ester group.

9. A pharmaceutical composition comprising a compound of formula I

 (I)

where n is an integer having a value of 4 to 12;

$R^1$ is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group —$CHR^3$—O—CO—$R^2$;

each $R^2$ independently is an optionally unsaturated $C_{1-15}$ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the $R^3$ to it is a 2 to 5 backbone atom bridging group;

and each $R^3$ independently is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group $R^2$—CO—O— or together with $R^2$ forms a 2 to 5 backbone atom bridging group, or a physiologically tolerable salt or ester thereof together with at least one pharmaceutical carrier or excipient.

10. A method of treatment of a human or non-human animal subject to combat acne, rocasea, hyperpigmentation, actinic keratoses, basal cell carcinoma, a bacterial infection, or skin cancer or to promote wound healing, the improvement comprising administering to said subject an effective amount of a compound of formula I

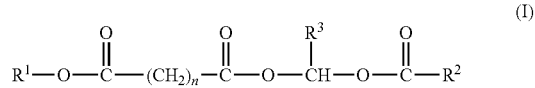 (I)

where n is an integer having a value of 4 to 12;

$R^1$ is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group —$CHR^3$—O—CO—$R^2$;

each $R^2$ independently is an optionally unsaturated $C_{1-15}$ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the $R^3$ gamma to it is a 2 to 5 backbone atom bridging group;

and each $R^3$ independently is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group $R^2$—CO—O— or together with $R^2$ forms a 2 to 5 backbone atom bridging group, or a physiologically tolerable salt thereof.

11. The method of claim 10, wherein the compound or the physiologically tolerable salt thereof is administered as a pharmaceutical composition comprising the compound or the physiologically tolerable salt thereof together with at least one pharmaceutical carrier or excipient.

12. The method of claim 10, wherein the alkane-dicarboxylic acid drug substance or physiologically tolerable salt or ester thereof is administered with one or more physiologically acceptable carriers or excipients.

13. A method of treating a human or non-human animal subject characterized by a condition wherein the condition is acne, rocasea, hyperpigmentation, a wound, actinic keratoses, basal cell carcinoma, a bacterial infection, or skin cancer, comprising administering to said subject a formulation comprising a compound of formula I

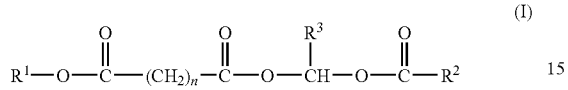

where n is an integer having a value of 4 to 12;

$R^1$ is hydrogen, an optionally unsaturated $C_{1-15}$ alkyl group optionally substituted with one or more of hydroxyl groups, oxo groups, halogenyl groups, alkoxy groups, acyloxy groups, thiol groups, amino groups, aromatic groups, alkylthio groups, and alkylamino groups, or is a group —$CHR^3$—O—CO—$R^2$;

each $R^2$ independently is an optionally unsaturated $C_{1-15}$ alkyl or alkoxy group, an aryl, alkaryl, aralkyl, aryloxy, alkaryloxy or aralkoxy group having up to 16 carbons, wherein any alkyl group is optionally substituted with one or more of hydroxyl groups, oxo groups, halogenyl groups, alkoxy groups, acyloxy groups, thiol groups, amino groups, aromatic groups, alkylthio groups, and alkylamino groups, or together with the $R^3$ gamma to it is a 2 to 5 backbone atom bridging group;

and each $R^3$ independently is hydrogen, an optionally unsaturated $C_{1-15}$ alkyl group optionally substituted wit one or more of hydroxyl groups, oxo groups, halogenyl groups, alkoxy groups, acyloxy groups, thiol groups, amino groups, aromatic groups, alkylthio groups, and alkylamino groups, or is a group $R^2$—CO—O— or together with $R^2$ forms a 2 to 5 backbone atom bridging group, or a physiologically tolerable salt thereof, and one or more physiologically acceptable carriers or excipients.

* * * * *

UNITED STATES PATENT AND TRADEMARK OFFICE
CERTIFICATE OF CORRECTION

| | | |
|---|---|---|
| PATENT NO. | : 7,629,383 B2 | Page 1 of 1 |
| APPLICATION NO. | : 10/496328 | |
| DATED | : December 8, 2009 | |
| INVENTOR(S) | : Jo Klaveness | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1050 days.

Signed and Sealed this

Second Day of November, 2010

David J. Kappos
*Director of the United States Patent and Trademark Office*